(12) United States Patent
James et al.

(10) Patent No.: US 7,744,737 B1
(45) Date of Patent: Jun. 29, 2010

(54) MICROFLUIDIC DEVICE FOR THE ASSEMBLY AND TRANSPORT OF MICROPARTICLES

(75) Inventors: Conrad D. James, Albuquerque, NM (US); Anil Kumar, Framingham, MA (US); Boris Khusid, New Providence, NJ (US); Andreas Acrivos, Stanford, CA (US)

(73) Assignee: Sandia Corporation, Albuquerque, NM (US)

( * ) Notice: Subject to any disclaimer, the term of this patent is extended or adjusted under 35 U.S.C. 154(b) by 150 days.

(21) Appl. No.: 12/028,907

(22) Filed: Feb. 11, 2008

Related U.S. Application Data

(60) Provisional application No. 60/952,023, filed on Jul. 26, 2007.

(51) Int. Cl.
*G01N 27/447* (2006.01)
*G01N 27/453* (2006.01)

(52) U.S. Cl. .................. 204/547; 204/632
(58) Field of Classification Search ............ 204/547, 204/643
See application file for complete search history.

(56) References Cited

U.S. PATENT DOCUMENTS

| | | | |
|---|---|---|---|
| 6,596,143 B1 * | 7/2003 | Wang et al. | 204/547 |
| 6,858,439 B1 * | 2/2005 | Xu et al. | 436/518 |

FOREIGN PATENT DOCUMENTS

WO      WO-0105514 A1 *  1/2001

OTHER PUBLICATIONS

Dawn J. Bennett et al, "Combined field-induced dielectrophoresis and phase separation for manipulating particles in microfluidics", Applied Physics Letters, vol. 83, No. 23, 2003, pp. 4866-4868.
Pei Yu Chiou et al, "Massively parallel manipulation of single cells and microparticles using optical images", Nature Publishing Group, vol. 436, 2005, pp. 370-372.
David G. Grier, "A revolution in optical manipulation," insight review articles, Nature Publishing Group, vol. 424, 2003, pp. 810-816.
T. P. Hunt et al, "Addressable micropost array for the dielectrophoretic manipulation of particles in fluid", Applied Physics Letters, 2004, vol. 85, No. 26, pp. 6421-6423.
Anil Kumar et al, "Conveyor-belt method for assembling microparticles into large-scale structures using electric fields", Applied Physics Letters, vol. 90, 2007, pp. 154104-1 through 154104-3.
S. Tsukahara et al, "Dielectrophoresis of microbioparticles in water with planar and capillary quadrupole electrodes", IEE Pro.-Nanobiotechnol, vol. 150, No. 2 2003, pp. 59-65.
J.J. Sniegowski et al, "IC-Compatible Polysilicon Surface Micromachining", Annu. Rev. Mater. Sci., 2000, vol. 30 pp. 299-333.

* cited by examiner

*Primary Examiner*—Alex Noguerola
(74) *Attorney, Agent, or Firm*—Kevin W. Bieg

(57) ABSTRACT

A microfluidic device comprising independently addressable arrays of interdigitated electrodes can be used to assembly and transport large-scale microparticle structures. The device and method uses collective phenomena in a negatively polarized suspension exposed to a high-gradient strong ac electric field to assemble the particles into predetermined locations and then transport them collectively to a work area for final assembly by sequentially energizing the electrode arrays.

15 Claims, 5 Drawing Sheets

MICROFLUIDIC DEVICE FOR THE ASSEMBLY AND TRANSPORT OF MICROPARTICLES

CROSS-REFERENCE TO RELATED APPLICATION

This application claims the benefit of U.S. Provisional Application No. 60/952,023, filed Jul. 26, 2007, which is incorporated herein by reference.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to microfluidics and, in particular, to a microfluidic device and method for the assembly and transport of microparticles.

BACKGROUND OF THE INVENTION

The assembly of microparticles into large-scale structures is a proven and efficient method for the fabrication of structured materials with relevance to a wide variety of devices for photonic, electronic, magnetic, and sensor applications. See M. Boncheva and G. M. Whitesides, *MRS Bull.* 30, 736 (2005); and G. M. Whitesides and B. Grzybowski, *Science* 295, 2418 (2002). In comparison with techniques that rely on the spontaneous self-organization of particles into desired patterns, the use of optical, acoustic, electric, and magnetic fields to trap and transport the particles offers a significantly higher level of precision for the control of the particle positions. See B. A. Grzybowski et al., *Nat. Mater.* 2, 241 (2003); P. J. Burke, *Nanodielectrophoresis: Electronic Nanotweezers, Encyclopedia of Nanoscience and Nanotechnology* Vol. 6, edited by H. S. Nalwa (American Scientific, Stevenson Ranch, Calif., 2004), pp. 623-641; M. Riegelman et al., *ASME J. Fluids Eng.* 128, 6 (2006); J. P. Hoogenboom et al., *Appl. Phys. Lett.* 80, 4828 (2002); W. D. Ristenpart et al., *Phys. Rev. Lett.* 90, 128303 (2003); and B. B. Yellen et al., *Proc. Natl. Acad. Sci. U.S.A.* 102, 8860 (2005). A characteristic feature of these field-based methods is that all of them utilize a force exerted by a strong field gradient on an individual particle to trap it in regions of minimum or maximum field strength. When such a trap is displaced, the gradient force thereby generated causes an entrapped particle to follow the trap motion. Although precise, these techniques are slow since they deliver particles to a work area one at a time. To speed up the process, techniques recently reported in the literature involve the parallel transportation of particles by creating and simultaneously translating multiple field traps which, however, still contain a single particle. See P. Y. Chiou et al., *Nature (London)* 436, 370 (2005); T. P. Hunt et al., *Appl. Phys. Lett.* 85, 6421 (2004); I. R. Perch-Nielsen et al., *Opt. Express* 13, 2852 (2005); and D. G. Grier, *Nature (London)* 424, 810 (2003).

Therefore, a need remains for a device and method to collectively assemble and transport microparticles to enable formation of large-scale structures.

SUMMARY OF THE INVENTION

The present invention is directed to a microfluidic device for assembling and transporting microparticles, comprising a channel formed on a substrate for flow of a fluid therein, the fluid comprising a negatively polarizable suspension of microparticles in a liquid; at least two arrays of independently addressable electrodes disposed successively in the channel; means for applying different ac voltages to the at least two arrays of independently addressable electrodes to generate a high-gradient electric field within the channel, thereby causing the microparticles to concentrate in regions of low field strength in the channel; and means for moving the high-gradient electric field within the channel by modifying the sequence of applying the ac voltages to the at least two arrays of independently addressable electrodes. The microfluidic device preferably comprises at least three arrays of independently addressable electrodes to enable directional control of the particle transport. The electrode arrays can comprise interdigitated electrodes. The electrodes can be substantially planar and substantially parallel. The height of the channel can be less than 100 microns.

The invention is further directed to a method for assembling and transporting microparticles, comprising providing a microfluidic device for assembling and transporting microparticles; applying different voltages to the at least two arrays of the microfluidic device, thereby causing the microparticles to assemble in regions of low field strength in the channel; and modifying the sequencing of the ac voltages applied to the at least two arrays, thereby causing the microparticles to be transported to modified regions of low field strength in the channel.

The action of collective phenomena in the suspension of negatively polarized particles exposed to a sufficiently strong high-gradient ac field enables the assembly of distinct particle structures which can then be transported by sequentially energizing and grounding microelectrodes. The device and method can be used to build large-scale microparticle structures by forming unit blocks and then transporting them to specific locations for further assembly and/or processing such as in situ polymerization of structures in a matrix.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

FIG. 2a shows two arrays of interdigitated electrodes that are independently addressable. FIG. 2b shows four arrays of interdigitated electrodes that are independently addressable. FIG. 2c shows an electrode configuration that enables assembled particles to be redirected around a bend in a channel. FIG. 2d shows an electrode configuration that enables particles be to focused or defocused, depending on the transport direction.

FIG. 3a shows a 1% (v/v) suspension of latex beads above the electrodes. FIG. 3b shows the beads concentrated into columns (seen as white) in the low-field regions caused by energizing the first electrode array with a 5 $V_{rms}$ and 1 MHz ac voltage and grounding the second array. FIG. 3c shows the beads moved to another low-field region by grounding the first array and energizing the second array.

FIG. 3d shows the columns formed by energizing the first array and grounding the second array. FIG. 3e shows the beads transported to another low field region by grounding the first array and energizing the second array and by flowing the fluid with a velocity of 4.3 μm/s in the channel. FIG. 3f shows the bead columns destabilized at a fluid velocity of 700 μm/s.

FIG. 5a shows the beads concentrated into columns (seen as white) in the low-field regions by applying a 7.5 $V_{rms}$ and 1 MHz voltage to the first, second, and fourth electrode arrays and grounding the third array. FIG. 5b shows the beads moved to another low-field region by disconnecting the second and third arrays. FIG. 5c shows the beads moved further by leaving the second array grounded and applying voltage to the third array.

DETAILED DESCRIPTION OF THE INVENTION

Particles experience both an electrophoretic force and a dielectrophoretic force when exposed to a spatially nonuniform electric field. The electrophoretic force, being the time-average of the product of the particle charge and the field strength, vanishes in an ac field of sufficiently high frequency. However, the dielectrophoretic force, being the product of the particle dipole moment and the gradient of the field strength, remains effective in high-frequency fields because the dielectrophoretic force averaged over the field oscillations gives a nonzero value. If a particle is negatively polarized relative to the liquid, it will move toward a region of low field strength (negative dielectrophoresis, or nDEP). Therefore, high-gradient ac electric fields can be used to aggregate suspended particles. In particular, interparticle electric and hydrodynamic interactions, if sufficiently strong, can cause a negatively polarized suspension of initially uniform concentration to undergo a separation into low- and high-concentrated phases and to form a distinct front between regions enriched with and depleted of particles. See D. J. Bennett et al., *Appl. Phys. Lett.* 83, 4866 (2003); and A. Kumar et al., *Phys. Rev. E* 69, 021402 (2004), which are incorporated herein by reference.

Figure 1A:
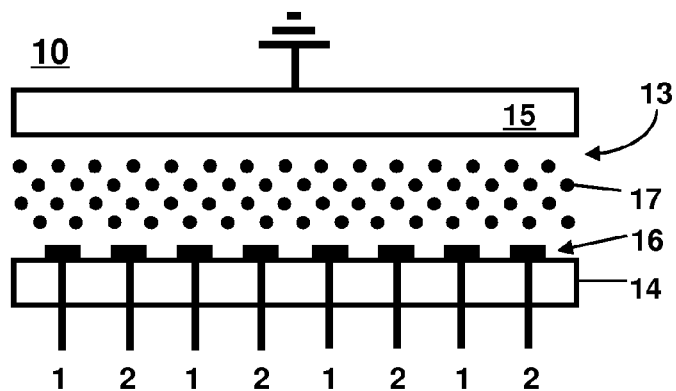
FIGS. 1a-1c are side-view schematic illustrations of a microfluidic device comprising two arrays of independently addressable electrodes that can be used to assemble and transport large-scale multiparticle structures.
Figure 1B:
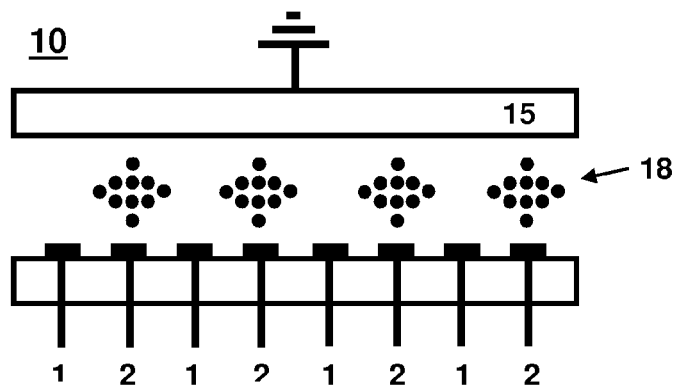
Figure 1C:
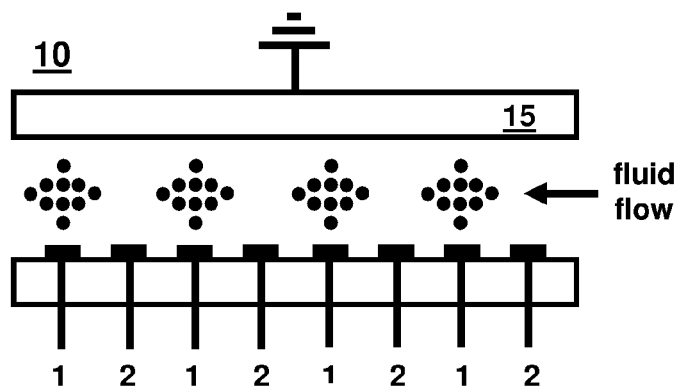

The device of the present invention relies on these collective phenomena in a negatively polarized suspension subject to a high-gradient ac electric field to assemble and transport microparticles. FIGS. 1a-1c show side-view schematic illustrations of a microfluidic device 10 of the present invention. The microfluidic device 10 comprises a channel 13 formed on a substrate 14 for flow of a fluid therein. The channel further comprises a top wall 15 and side walls (not shown). The fluid comprises microparticles 17 that can be assembled and transported by the microfluidic device 10. For example, the channel 13 can be formed on a silicon substrate from a plurality of deposited and patterned layers of polycrystalline silicon and silicon nitride, using surface micromachining processes. See Galambos et al., U.S. Pat. No. 6,797,187; M. Okandan et al., *Proc. SPIE* 4560, 133 (2001); and J. J. Sniegowski and M. P. de Boer, *Ann. Rev. Mater. Sci.* 30, 299 (2000), which are incorporated herein by reference. Alternatively, other microfabrication processes and materials can be used to fabricate the microfluidic device 10, as will be apparent to those skilled in the art. The channel 13 can typically have a lateral dimension of millimeters and a height of about 100 μm or less, since the DEP force decreases with distance from the electrodes. The channel 13 comprises a plurality of electrodes 16 for generating an electrical potential within the channel 13 in response to ac voltages applied to the electrodes, with the voltages generally being about 20 rms volts or less with frequencies typically between 0.5 to 30 MHz. The electrodes 16 can be substantially planar, substantially parallel, oriented substantially perpendicular to the direction of fluid flow, and spaced along the length of the channel 13. The electrodes 16 can typically have widths of less than one micron to tens of microns and can spaced apart by similar distances. The electrodes 16 can be formed from any electrically-conductive material, such as polycrystalline silicon, a metal or a metal alloy, or carbon. Electrical wiring can be formed through and underneath the substrate 14 for electrical activation of the electrodes 16. The top wall 15 of the channel can be a conducting or non-conducting layer. The top wall 15 can be grounded (as shown), energized with an applied voltage, or can further comprise additional energized electrodes (not shown) to modify the ac field configuration within the channel 13.

As shown in FIG. 1a, the fluid can initially comprise a uniform suspension of neutrally buoyant microparticles 17 in a liquid. As described by Bennett and Kumar, when exposed to the spatially non-uniform electric field generated by electrodes, a particle suspended in a fluid in a channel will polarize and interact with the electric field, generating a time-averaged dielectrophoretic force, $F_{DEP}$, which is given by:

$$F_{DEP} = \frac{3}{2}\varepsilon_0\varepsilon_f V_p Re(\beta^*(\omega))\nabla E_{rms}^2 \quad (1)$$

where $\epsilon_0$ and $\epsilon_f$ are the vacuum and fluid permittivity, respectively, $V_p$ is the particle volume, $Re(\beta^*(\omega))$ is the real component of the relative particle polarization $\beta^*(\omega)$ at frequency $\omega$, and $\nabla E_{rms}^2$ is the gradient of the squared root-mean-square electric field. The electric field must be non-uniform ($\nabla E_{rms}^2 \neq 0$), and a difference in the polarizabilities between the particle and the fluid must exist in order for particle motion to occur by DEP. The gradient in the electric field leads to a nonsymmetrical dipole in the particle. This produces a net force on the particle accompanied by motion. If the particle is less polarizable than the fluid ($Re(\beta^*(\omega))<0$), the particle will migrate towards regions of low $\nabla E_{rms}^2$. The DEP effect operates in aqueous solutions, such as DI water, or solvents, such as isopropanol. The types of particles that can be manipulated are typically insulating particles, such as polystyrene, silica, or latex, or conducting metallic particles. Also, the surface charge on the particle typically dominates the DEP response. Therefore, surface functionalization of the particles can enhance the DEP effect. As Eq. (1) implies, the strength of the DEP force will also depend on the electrode configuration and the voltage differential applied to successive adjacent electrodes. The higher the voltage differential, the faster, tighter, and more stable is the particle assembly. Typically, for electrodes spaced tens of microns apart, the difference in voltages between adjacent electrodes can be three or more volts. For example, an intermediate electrode can be grounded and spaced between high voltage electrodes. With such an electrode configuration, preferably the top wall is also grounded.

The DEP effect is frequency dependent, with higher frequencies having more likelihood of providing a significant dielectrophoretic force. In the radio frequency range, the relative polarizability of a particle immersed in a fluid is mainly influenced by the ratio of capacitances of the particle and the fluid, so that a reasonable estimate of Re(β*) is given by:

$$Re(\beta^*) \approx \frac{\varepsilon_p - \varepsilon_f}{\varepsilon_p + 2\varepsilon_f}. \tag{2}$$

where $\varepsilon_p$ is the particle permittivity. For example, deionized (DI) water has a moderate polarizability, while insulating materials such as latex or silica have low polarizability. The critical frequency at which the particle-media system will transition from being dominated by the conductivities of the system to being dominated by the permittivities is given by the Maxwell-Wagner frequency:

$$f_{MW} = \frac{\sigma_p + 2\sigma_f}{2\pi(\varepsilon_p + 2\varepsilon_f)} \tag{3}$$

where $\sigma_p$ and $\sigma_f$ are the particle and fluid conductivities, respectively, and $\varepsilon_p$ and $\varepsilon_f$ are the corresponding permittivities. Therefore, an ac field in the radiofrequency range is preferably employed to limit undesirable electric effects in water, such as electrolysis, electroosmosis, and electroconvection. Elimination of these undesirable electrical effects using MHz frequencies therefore allows the use of larger voltage amplitudes.

As shown in FIG. 1b, multiparticle structures 18 can be assembled in a negatively polarized suspension of initially uniform concentration by exposing the suspension to an ac field configuration. In the example shown, an ac voltage can be applied to electrodes 1 and electrodes 2 can be grounded. This creates a region of low field strength in the channel above the grounded electrodes 2. The ac field configuration concentrates essentially all the particles into the focused low-field regions that are separated from the particle-free regions by sharp interfaces.

As shown in FIG. 1c, in order to transport these structures, another ac field configuration can be created in which the arrangement of the energized and grounded electrodes is modified (e.g., electrodes 2 are energized and electrodes 1 are grounded). Since the local suspension viscosity increases sharply with particle concentration, the relative velocity of a particle within the concentrated suspension already assembled is small. Therefore, the assembled suspension moves as a whole to a new low-field strength region (i.e., to above grounded electrodes 1), provided that the magnitude of the driving electric and hydrodynamic forces is sufficiently small to prevent the sharp interfaces from disintegrating.

Figure 2B:
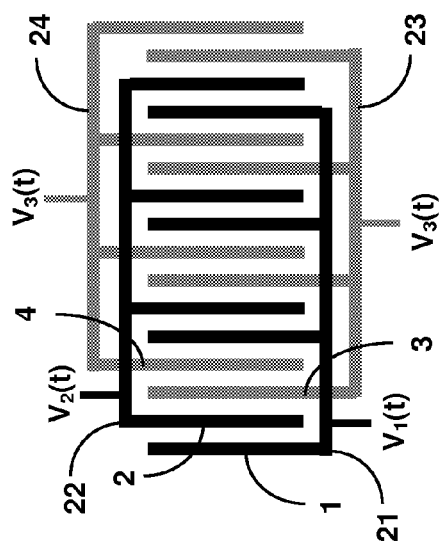
FIGS. 2a-2d are top-view schematic illustrations of exemplary electrode configurations.
Figure 2D:
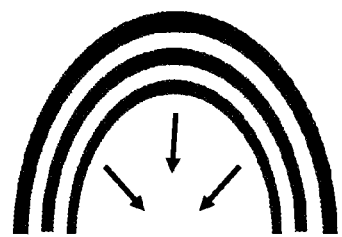
Figure 2A:
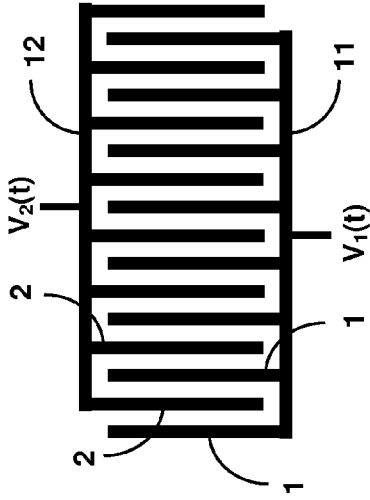
Figure 2C:
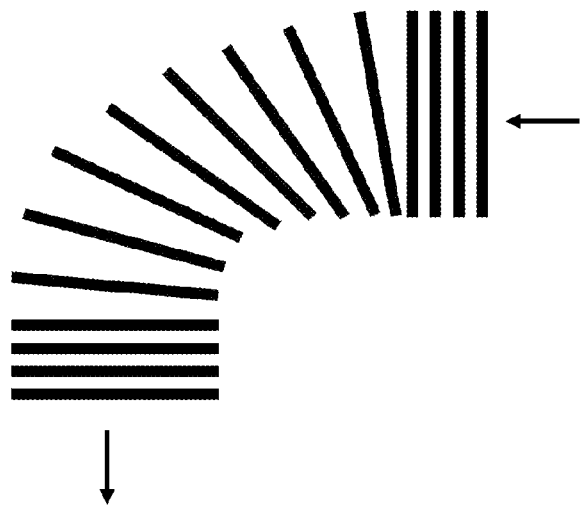

The electrodes 16 can be arranged in a variety of configurations. FIGS. 2a-2d show top-view schematic illustrations of exemplary configurations. For example, the electrode configuration can comprise an interdigitated electrode configuration. The exemplary interdigitated electrode configuration shown in FIG. 2a comprises two arrays of interdigitated electrodes 11 and 12 that are independently addressable via electrical connections at the opposing forked ends of the interdigitated electrodes. In this configuration, ac voltages $V_1(t)$ and $V_2(t)$ can be applied independently to each array of interdigitated electrodes 11 and 12, to energize successive finger electrodes 1 and 2, respectively. FIG. 2b shows an alternative interdigitated electrode configuration comprising four arrays of interdigitated electrodes 21, 22, 23, and 24. In this configuration, each successive set of finger electrodes 1, 2, 3, and 4 are energized separately by ac voltages $V_1(t)$, $V_2(t)$, $V_3(t)$, and $V_4(t)$ applied to the interdigitated electrode arrays 21, 22, 23, and 24, respectively. The electrodes can also be shaped to redirect or focus the assembled particles, so long as adjacent electrodes remain substantially parallel to enable particles to be assembled and transported. For example, FIG. 2c shows an electrode configuration that enables assembled particles to be redirected, around a bend in a channel. FIG. 2d shows an electrode configuration that enables particles be to focused or defocused, depending on the transport direction. As will be apparent to those skilled in the art, alternative electrode structures and electrode energizing configurations can be used to provide alternative assembly and transport characteristics.

To demonstrate the ability to assemble and then transport such particle structures, experiments were performed in microfluidic devices mounted on a micromanipulator. A microscope was used to check the alignment of the top and bottom channel walls and to measure the channel height between them. A conducting and transparent indium titanium oxide (ITO) glass slide (surface resistivity of 10 $\Omega/cm^2$) was used as the top wall (the ITO coating was on the inner side of the slide). The suspensions were prepared by diluting, with deionized water (pH of 5.5-6.0 and conductivity of 0.55 μS/cm as measured using a dc conductivity meter), a 10% (by weight) aqueous solution of latex beads (particle diameter 3.1 particle density 1.05 g/cm$^3$) that were introduced into the channel using a microsyringe.

A manual multielectrode switch was used to connect simultaneously the desired sets of the microelectrodes to either a grounding connector or to the voltage output of a function generator. All the energized electrodes were supplied with the same voltage signal and were alternated with grounded electrodes in order to vary the field strength in the channel space. The operating frequencies used were in the megahertz range to suppress undesirable field effects, such as electro-osmosis, electroconvection, and electrolysis. The real part of the relative polarizability of the latex beads in water within this frequency range was Re(β)~−0.45. Therefore, the suspensions were negatively polarized. The application of an ac voltage to the electrode arrays of the microfluidic channel caused the particles to accumulate in the low-field regions located above the grounded electrodes and to assemble into distinct cylindrical columns. In order to transport the assembled cylinders, the accumulated particles must be tightly bound within the low field region. This was achieved both by grounding the conducting channel top wall as well as by decreasing the height of the channel between the top and the bottom walls so that the field generated near the top wall was sufficiently strong to push the nearby particles toward the midplane of the channel. Under these conditions, changing the order of energizing and grounding the electrodes caused the assembled cylinders to move to another location of the low-field regions.

Figure 3:
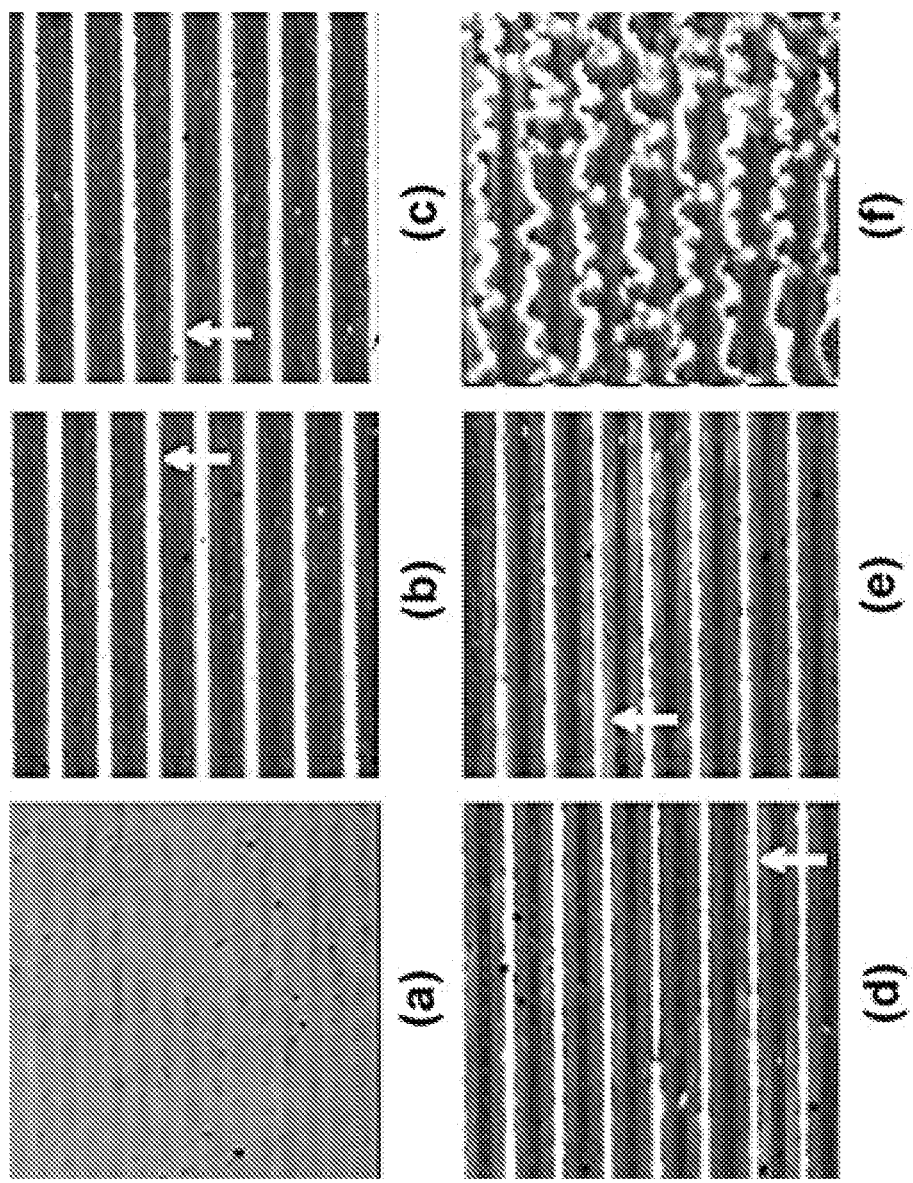
FIGS. 3a-3f are top-view photographs of the time evolution of the particle distributions in a microfluidic device comprising two arrays of interdigitated electrodes that are independently addressable.

The first microfluidic device comprised two independently addressable interdigitated electrode arrays configured as shown in FIGS. 1a-1c and FIG. 2a (i.e., an array 11 comprising finger electrodes 1, and another array 12 comprising finger electrodes 2). The interdigitated arrays comprised a total of 100 gold finger electrodes. The width and the interelectrode spacing of the finger electrodes were both 20 μm. The interdigitated arrays were alternately connected to a high voltage and to ground. FIGS. 3a-3f are top-view photographs of the time evolution of the particle distributions, taken through the transparent ITO top wall of the microfluidic channel. The linear electrodes are oriented horizontally, with the fluid flow from bottom to top in the photos. The channel height was about 100 μm for the channel in FIGS. 3a-3c and about 50 μm for the channel in FIGS. 3d-3f. As shown in FIG. 3a, the latex beads in a 1% (v/v) suspension were initially uniformly distributed in the channel. As shown in FIG. 3b, the dielectrophoretic force created by connecting adjacent interdigitated electrode arrays to high voltage (5 $V_{rms}$ and 1 MHz) and to ground caused the latex beads to concentrate into distinct ~20% (v/v) cylindrically-shaped columns (seen as white lines in the photos) located in the low-field regions above the grounded electrodes. Alternating the energizing and grounding sequence of the two arrays caused the latex beads to travel simultaneously with an average velocity of ~300 μm/s to adjacent low-field regions created by the sequencing (shown by the arrows in FIGS. 3b and 3c). The transport time can be further reduced by increasing the electric field strength and sequencing speed. However, control of the direction of the column motion was determined by the presence of some asymmetry in the fluid flow and, therefore, varied from experiment to experiment and sometimes within an ongoing experiment. But, by slowly translating the chip (up to ~200 μm/s) using the manipulator stage to generate a shear flow in the channel while maintaining the original energized sequence of the device electrodes, it was possible to transport the columns in the desired direction, as shown in FIGS. 3d and 3e. However, a faster motion of the device destabilized the columns, as shown in FIG. 3f.

Figure 4A:
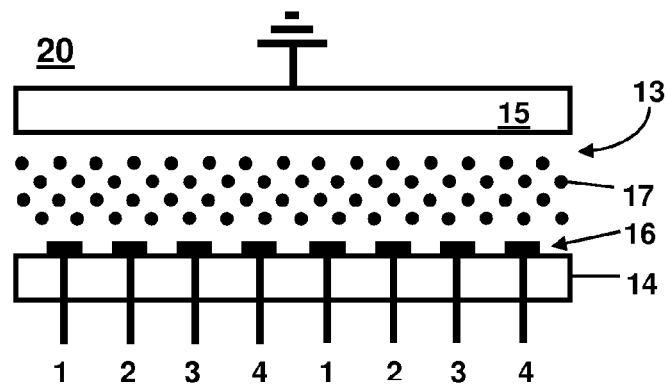
FIGS. 4a-4d show side-view schematic illustrations of a microfluidic device comprising four arrays of independently addressable electrodes that can be used to assemble and transport large-scale multiparticle structures.
Figure 4B:
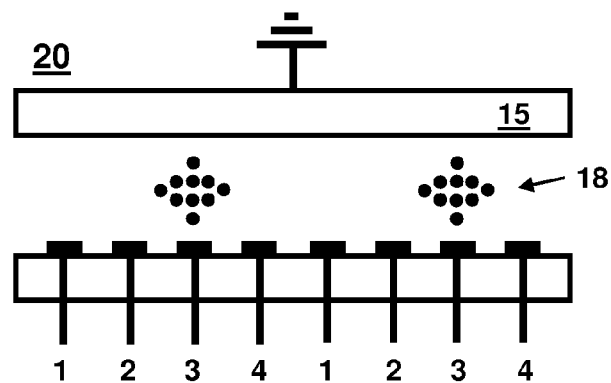
Figure 4C:
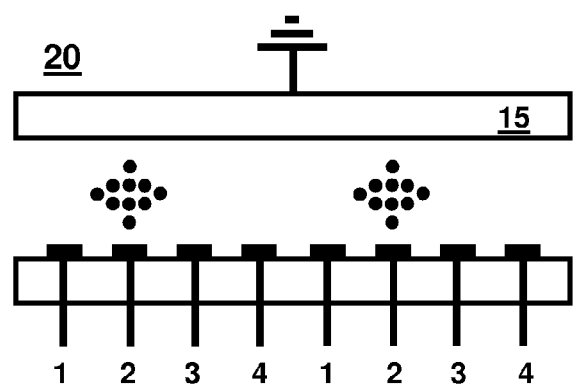
Figure 4D:
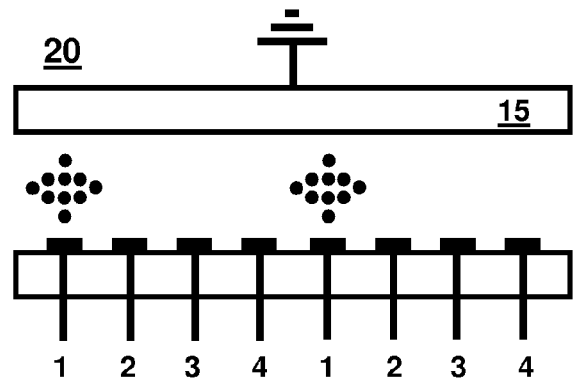

The second microfluidic device comprised four arrays of interdigitated electrodes as shown FIGS. 4a-4d and FIG. 2b (i.e., array 21 comprising finger electrodes 1, array 22 comprising finger electrodes 2, array 23 comprising finger electrodes 3, and array 24 comprising finger electrodes 4). This four-array configuration enables directional control of the particle transport without fluid flow. As shown in FIG. 4a, the fluid can initially comprise a uniform suspension of neutrally buoyant microparticles 17 in a liquid. As shown in FIG. 4b, multiparticle structures 18 can be assembled in a negatively polarized suspension of initially uniform concentration by exposing the suspension to an ac field configuration. In the example shown, an ac voltage is applied to electrodes 1, 2, and 4, and electrodes 3 are grounded. This creates a region of low field strength in the channel above the grounded electrodes 3. As shown in FIG. 4c, in order to transport these structures, another ac field configuration is created in which the arrangement of the energized and grounded electrodes is modified (e.g., electrodes 1, 3, and 4 are energized and electrodes 2 are grounded). Since electrodes 4 remain energized, the particles are forced to move in a controlled direction to the region of low field strength above the grounded electrodes 2. The transport can be continued by again modifying the ac field configuration by energizing electrodes 2, 3, and 4 and grounding electrodes 1, as shown in FIG. 4d. As will be apparent, the assembling particles can be transported in either direction by appropriate sequencing of energized and grounded electrodes. As will also be apparent, at least three independently addressable electrode arrays are necessary to transport the assembled particles without the influence of fluid flow or other external force.

Figure 5:
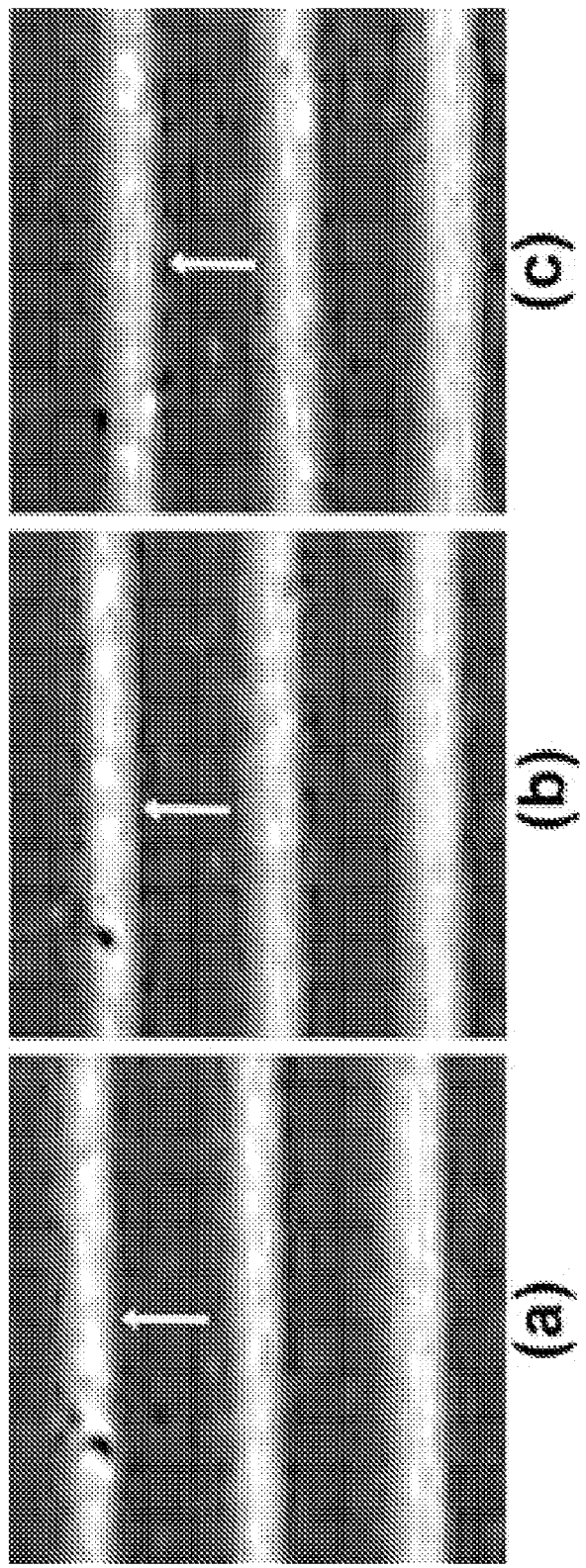
FIGS. 5a-5c are top-view photographs of the time evolution of the particle distributions in a microfluidic device comprising four arrays of independently-addressable interdigitated electrodes.

The second microfluidic device was fabricated using surface micromachining. This process uses conductive p-doped polycrystalline silicon thin-film electrodes on top of insulated silicon wafers. The microfluidic device comprised 24 finger electrodes (the electrode width and interelectrode spacing were both 10 μm) arranged into four arrays of interdigitated arrays. This configuration enabled independently addressing of every four successive finger electrodes. The channel height was approximately 50 μm. As shown in FIGS. 5a-5c, the columns could be transported in the desired direction without generating a shear flow by choosing an appropriate energizing sequence of the electrode arrays. Specifically, as shown in FIG. 5a, the application of 7.5 $V_{rms}$ and 1 MHz ac voltage to the first, second, and fourth electrode arrays and the grounding of third array caused the latex beads in an initially uniform 2% (v/v) suspension to concentrate into distinct ~20% (v/v) columns located in the low-field regions above the electrodes of grounded third array. As shown in FIG. 5b, by disconnecting the second and third arrays while maintaining the first and fourth arrays at their original voltage (the voltages on the floating second and third arrays in this configuration were measured to be approximately 1 $V_{rms}$) caused the columns to move simultaneously with an average velocity of ~140 μm/s to a region halfway between the electrodes of second and third arrays. Finally, as shown in FIG. 5c, by grounding the second array and applying 7.5 $V_{rms}$ to the third array while still maintaining the first and fourth arrays at their original voltage, the columns were made to move over to the region above the electrodes of grounded second array with average velocity ~140 μm/s. The columns were transported in the reverse direction (i.e., from being located above the electrodes of the second array to above the electrodes of the third array) by repeating the process just described but in the opposite direction. The overall process of column transport between the electrodes of these two arrays was repeated several times.

The present invention has been described as a microfluidic device for assembly and transport of microparticles. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A microfluidic device for assembling and transporting microparticles, comprising:
    a channel formed on a substrate for flow of a fluid therein, the fluid comprising a negatively polarizable suspension of microparticles in a liquid;
    at least two arrays of independently addressable electrodes disposed successively in the channel;
    means for applying ac voltages of different magnitudes to the at least two arrays of independently addressable electrodes to generate a high-gradient electric field within the channel, thereby causing the microparticles to concentrate in regions of low field strength in the channel; and
    means for moving the high-gradient electric field within the channel by sequencing the application of the ac voltages of different magnitudes to the at least two arrays of independently addressable electrodes.

2. The microfluidic device of claim 1, wherein the electrodes comprise at least three arrays of independently addressable electrodes.

3. The microfluidic device of claim 1, wherein the at least two arrays of independently addressable electrodes comprise interdigitated electrodes.

4. The microfluidic device of claim 1, wherein the at least two arrays of independently addressable electrodes comprise four arrays of interdigitated electrodes that are independently addressable.

5. The microfluidic device of claim 1, wherein the electrodes of the at least two arrays are substantially planar and substantially parallel.

6. The microfluidic device of claim 1, wherein the height of the channel is less than 100 microns.

7. The microfluidic device of claim 1, wherein the ac voltage comprises a frequency of 0.5 to 30 MHz.

8. The microfluidic device of claim 1, wherein the ac voltage difference between successive electrodes is greater than 3 rms volts.

9. The microfluidic device of claim 1, wherein the at least two arrays of independently addressable electrodes are disposed on a top or a bottom wall of the channel.

10. The microfluidic device of claim 9, wherein the wall opposite the top or bottom wall on which the independently addressable electrodes are disposed is non-conducting.

11. The microfluidic device of claim 9, wherein the wall opposite the top or bottom wall on which the independently addressable electrodes are disposed is conducting.

12. The microfluidic device of claim 11, wherein the conducting wall is grounded.

13. The microfluidic device of claim 11, wherein the conducting wall is energized with an applied voltage.

14. The microfluidic device of claim 9, wherein the wall opposite the top or bottom wall on which the independently addressable electrodes are disposed comprises additional energized electrodes.

15. A method for assembling and transporting microparticles, comprising:

provided a microfluidic device for assembling and transporting microparticles, wherein the microfluidic device comprises:

a channel formed on a substrate for flow of a fluid therein, the fluid comprising a negatively polarizable suspension of microparticles in a liquid;

at least two arrays of independently addressable electrodes disposed in the channel wherein the electrodes of the at least two arrays are configured successively in the channel; and means for applying ac voltages of different magnitudes to the at least two arrays of independently addressable electrodes to generate a high-gradient electric field within the channel;

applying different voltages to the at least two arrays thereby causing the microparticles to assemble in regions of low field strength in the channel; and sequencing the application of the ac voltages of different magnitudes to the at least two arrays, thereby causing the microparticles to be transported to sequenced regions of low field strength in the channel.

* * * * *